(12) United States Patent
Chern et al.

(10) Patent No.: US 7,939,523 B2
(45) Date of Patent: May 10, 2011

(54) IMIDAZOLIDINONE AND IMIDAZOLIDINETHIONE DERIVATIVES

(75) Inventors: Jyh-Haur Chern, Taipei (TW); Tsu-An Hsu, Taipei (TW); Iou-Jiun Kang, Pingtung County (TW); Li-Wen Wang, Kaohsiung (TW); Chung-Chi Lee, Chung-He (TW); Yen-Chun Lee, Taitung (TW); Yen-Shian Wu, Kaohsiung (TW); Sheng-Ju Hsu, Yangmei Town (TW); Yueh Andrew Yueh, Xindian (TW); Yu-Sheng Chao, Warren, NJ (US)

(73) Assignee: National Health Research Institutes, Miaoli County (TW)

( * ) Notice: Subject to any disclaimer, the term of this patent is extended or adjusted under 35 U.S.C. 154(b) by 208 days.

(21) Appl. No.: 12/348,480

(22) Filed: Jan. 5, 2009

(65) Prior Publication Data
US 2009/0176766 A1    Jul. 9, 2009

Related U.S. Application Data

(60) Provisional application No. 61/019,663, filed on Jan. 8, 2008.

(51) Int. Cl.
| A61K 31/4166 | (2006.01) |
| A61K 31/4178 | (2006.01) |
| A61K 31/4439 | (2006.01) |
| A61K 31/513 | (2006.01) |
| A61K 31/551 | (2006.01) |
| C07D 243/04 | (2006.01) |
| C07D 239/10 | (2006.01) |
| C07D 233/30 | (2006.01) |
| C07D 401/04 | (2006.01) |

(52) U.S. Cl. ........ 514/218; 514/256; 514/341; 514/392; 540/553; 540/492; 544/315; 546/274.4; 548/316.4

(58) Field of Classification Search .................. None
See application file for complete search history.

(56) References Cited

U.S. PATENT DOCUMENTS
| 4,221,817 A | 9/1980 | Tenne |
| 6,521,614 B1 * | 2/2003 | Maduskuie et al. .......... 514/218 |
| 6,696,487 B2 | 2/2004 | Gerusz et al. |
| 7,094,807 B2 | 8/2006 | Chen et al. |
| 7,102,007 B2 | 9/2006 | Aebi et al. |
| 2005/0032849 A1 | 2/2005 | Phadke et al. |
| 2005/0228013 A1 | 10/2005 | Thurkauf et al. |
| 2006/0025416 A1 | 2/2006 | Phadke et al. |

FOREIGN PATENT DOCUMENTS
| JP | 2005/330284 A2 | 2/2005 |
| JP | 2005/144790 | 5/2005 |
| WO | WO 99/40088 | 8/1999 |
| WO | WO2004/046095 | 6/2004 |
| WO | WO 2004052852 A1 * | 6/2004 |
| WO | WO2004/096210 | 11/2004 |
| WO | WO2005/095345 | 10/2005 |
| WO | WO2006/122011 | 11/2006 |
| WO | WO 2007065939 A1 * | 6/2007 |

OTHER PUBLICATIONS

Cory et al., "Use of an Aqueous Soluble Tetrazolium/Formazan Assay for Cell Growth Assays in Culture," *Cancer Communications*, vol. 3, No. 7, (1991).
Honda et al., Chem. Abst. 135 357776 (2001).
Willson et al. Chem. Abst. 118: 212577 (1993).
Bennett et al., J. Am Chem Soc. 1953 75(23); 6039-6040.

* cited by examiner

*Primary Examiner* — Yong Chu
*Assistant Examiner* — Michael Barker
(74) *Attorney, Agent, or Firm* — Occhiuti Rohlicek & Tsao LLP

(57) ABSTRACT

Imidazolidinone and imidazolinethione compounds of formula (I):

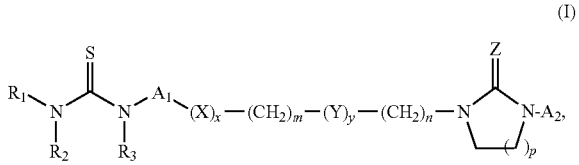

wherein $R_1$, $R_2$, $R_3$, $A_1$, $A_2$, X, Y, Z, m, n, p, x, and y are defined herein. Also disclosed is a method of treating hepatitis C virus infection with these compounds.

28 Claims, No Drawings

IMIDAZOLIDINONE AND IMIDAZOLIDINETHIONE DERIVATIVES

CROSS REFERENCE TO RELATED APPLICATIONS

This application claims priority to U.S. Provisional Application Ser. No. 61/019,663 filed Jan. 8, 2008. The contents of the prior application are hereby incorporated by reference in their entireties.

BACKGROUND

Hepatitis C virus (HCV) infection is estimated to affect 170 million individuals worldwide. This disease is primarily transmitted through contaminated blood products. Although its spread has been slowed as a result of improvement in blood screening in many countries, it remains the leading cause of liver disease-related deaths in the world. For example, it causes about 10,000 deaths annually in the U.S. alone. In the absence of effective therapies, the death rate is expected to triple over the next 2 decades. Current treatments based on interferon-alpha have low success rates, particularly for genotype-1 infections predominant in Europe, Japan, and the U.S. Also, they are expensive and poorly received by patients. Thus, there is a need to develop better therapeutic agents for treating HCV infection.

SUMMARY

This invention is based on the discovery that certain imidazolidinone and imidazolinethione compounds are effective in treating hepatitis C virus infection.

In one aspect, this invention relates to a compound of formula (I):

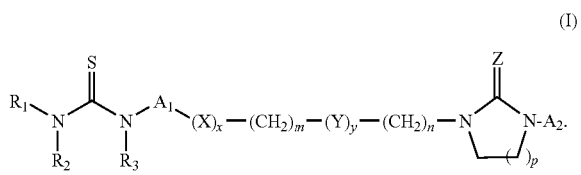

(I)

In formula (I), each of $R_1$, $R_2$, and $R_3$, independently, is H, alkyl, alkenyl, alkynyl, cycloalkyl, cycloalkenyl, heterocycloalkyl, heterocycloalkenyl, aryl, or heteroaryl; or $R_1$ and $R_2$, together with the nitrogen atom to which they are bonded, are heterocycloalkyl; or $R_2$ and $R_3$, together with the two nitrogen atoms to which they are bonded and the carbon atom bonded to both of the two nitrogen atoms, are heterocycloalkyl; each of $A_1$ and $A_2$, independently, is aryl or heteroaryl; each of X and Y, independently, is O, S, SO, $SO_2$, $N(R_a)$, $C(R_aR_b)$, C(O), C(O)O, $C(O)NR_a$, $NR_aC(O)NR_b$, $NR_aC(S)NR_b$, $NR_aC(O)O$, $SO_2NR_a$, alkylene, alkenylene, alkynylene, cycloalkylene, heterocycloalkylene, cycloalkenylene, heterocycloalkenylene, arylene, or heteroarylene, in which each of $R_a$ and $R_b$, independently, is H, alkyl, cycloalkyl, heterocycloalkyl, aryl, or heteroaryl; Z is O or S; each of m and n, independently, is 0, 1, 2, 3, 4, or 5; p is 1, 2, or 3; and each of x and y, independently, is 0 or 1.

One subset of the above-described imidazolidinone and imidazolinethione compounds includes those in which X is O and x is 1. In these compounds, $A_1$ can be 1,3-phenylene; $A_2$ can be phenyl, pyridyl, or naphthyl optionally substituted with halo, alkoxy, aryloxy, alkyl, cycloalkyl, aryl, or heteroaryl; each of $R_1$, $R_2$, and $R_3$ can be H; or Y can be 1,4-phenylene and y can be 0 or 1.

Another subset of the imidazolidinone and imidazolinethione compounds includes those in which $A_1$ is 1,3-phenylene and $A_2$ is phenyl, pyridyl, or naphthyl optionally substituted with halo, alkoxy, aryloxy, alkyl, cycloalkyl, aryl, or heteroaryl. In these compounds, each of $R_1$, $R_2$, and $R_3$ can be H.

The term "alkyl" refers to a straight or branched monovalent hydrocarbon containing 1-20 carbon atoms (e.g., $C_1$-$C_{10}$). Examples of alkyl include, but are not limited to, methyl, ethyl, n-propyl, i-propyl, n-butyl, i-butyl, and t-butyl. The term "alkylene" refers to a straight or branched bivalent hydrocarbon, containing 1-20 carbon atoms (e.g., $C_1$-$C_{10}$). Examples of alkylene include, but are not limited to, methylene and ethylene. The terms "alkenyl" and "alkenylene" respectively refer to a straight or branched monovalent and bivalent hydrocarbon containing 2-20 carbon atoms (e.g., $C_2$-$C_{10}$) and one or more double bonds. Examples of alkenyl and alkenylene include, but are not limited to, ethenyl, propenyl, propenylene, allyl, and 1,4-butadienyl. The terms "alkynyl" and "alkynylene" respectively refer to a straight or branched monovalent and bivalent hydrocarbon containing 2-20 carbon atoms (e.g., $C_2$-$C_{10}$) and one or more triple bonds. Examples of alkynyl and alkynylene include, but are not limited to, ethynyl, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, isobutoxy, sec-butoxy, and tert-butoxy.

The terms "cycloalkyl" and "cycloalkylene" respectively refer to a monovalent and a bivalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, cyclohexenyl, cycloheptyl, and cyclooctyl. The terms "cycloalkenyl" and "cycloalkenylene" respectively refer to a monovalent and a bivalent non-aromatic hydrocarbon ring system having 3 to 30 carbons (e.g., $C_3$-$C_{12}$) and one or more double bonds. Examples include cyclopentanyl, cyclohexanyl, and cycloheptanyl. The terms "heterocycloalkyl" and "heterocycloalkylene" respectively refer to a monovalent and a bivalent nonaromatic 5-8 membered monocyclic, 8-12 membered bicyclic, or 11-14 membered tricyclic ring system having one or more heteroatoms (such as O, N, S, or Se). Examples of heterocycloalkyl and heterocycloalkylene groups include, but are not limited to, piperazinyl, pyrrolidinyl, dioxanyl, morpholinyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds. The term "heterocycloalkenylene" refers to a bivalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "arylene" refers to a bivalent 6-carbon monocyclic, 10-carbon bicyclic, 14-carbon tricyclic aromatic ring system. The term "aryloxyl" refers to an —O-aryl. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "heteroarylene" refers to a bivalent aromatic 5-8 membered monocyclic, 8-12 membered bicyclic, or 11-14 membered tricyclic ring system having one or more heteroatoms (such as O, N, S, or Se).

Alkyl, alkenyl, alkynyl, cycloalkyl, heterocycloalkyl, cycloalkenyl, heterocycloalkenyl, aryl, heteroaryl, alkylene, alkenylene, alkynylene, cycloalkylene, heterocycloalkylene, cycloalkenylene, heterocycloalkenylene, arylene, and heteroarylene mentioned above include both substituted and unsubstituted moieties. Possible substituents on cycloalkyl, cycloalkenyl, heterocycloalkyl, heterocycloalkenyl, cycloalkylene, heterocycloalkylene, cycloalkenylene, heterocycloalkenylene, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, alkynyl, alkylene, alkenylene, or alkynylene include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In still another aspect, this invention relates to a method of treating HCV infection by administering to a subject infected with HCV an effective amount of one or more of the imidazolidinone and imidazolinethione compounds described above.

Also within the scope of this invention is a pharmaceutical composition containing one or more of the above-described imidazolidinone and imidazolinethione compounds for use in treating HCV infection, as well as this therapeutic use and use of the compounds for the manufacture of a medicament for treating HCV infection.

The details of one or more embodiments of the invention are set forth in the description below. Other features, objects, and advantages of the invention will be apparent from the description and the claims.

DETAILED DESCRIPTION

Shown in the table below are 26 exemplary compounds of this invention:

| | Structure | Name | M + 1 |
|---|---|---|---|
| 1 | 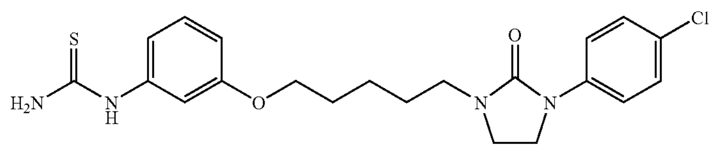 | (3-{5-[3-(4-Chloro-phenyl)-2-oxo-imidazolidin-1-yl]-pentyloxy}-phenyl)-thiourea | 433 |
| 2 | 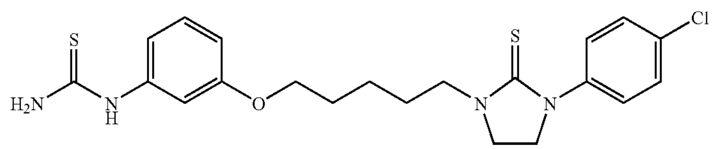 | (3-{5-[3-(4-Chloro-phenyl)-2-thioxo-imidazolidin-1-yl]-pentyloxy}-phenyl)-thiourea | 449 |
| 3 | 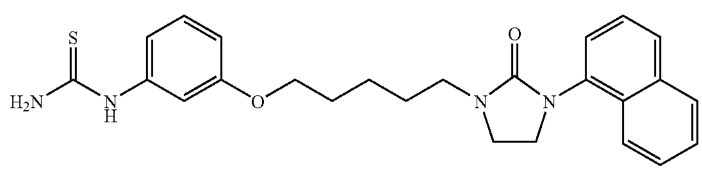 | {3-[5-(3-Naphthalen-1-yl-2-oxo-imidazolidin-1-yl)-pentyloxy]-phenyl}-thiourea | 449 |
| 4 | 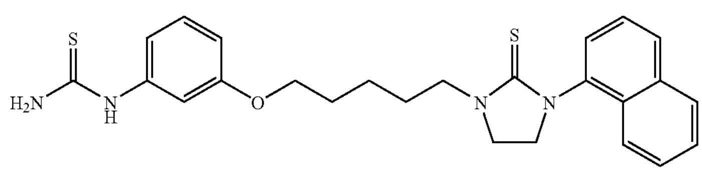 | {3-[5-(3-Naphthalen-1-yl-2-thioxo-imidazolidin-1-yl)-pentyloxy]-phenyl}-thiourea | 465 |
| 5 | 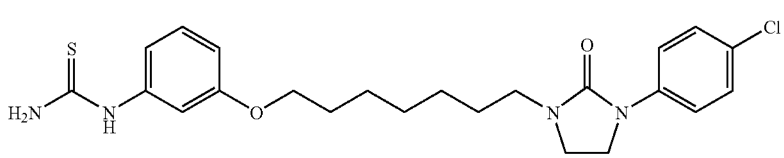 | (3-{7-[3-(4-Chloro-phenyl)-2-oxo-imidazolidin-1-yl]-heptyloxy}-phenyl)-thiourea | 461 |
| 6 | 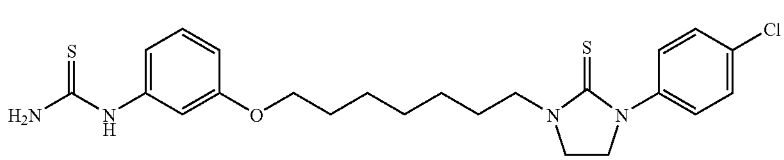 | (3-{7-[3-(4-Chloro-phenyl)-2-thioxo-imidazolidin-1-yl]-heptyloxy}-phenyl)-thiourea | 477 |

-continued

| | Structure | Name | M + 1 |
|---|---|---|---|
| 7 | 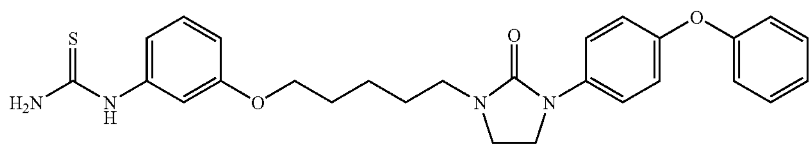 | (3-{5-[2-Oxo-3-(4-phenoxy-phenyl)-imidazolidin-1-yl]-pentyloxy}-phenyl)-thiourea | 491 |
| 8 | 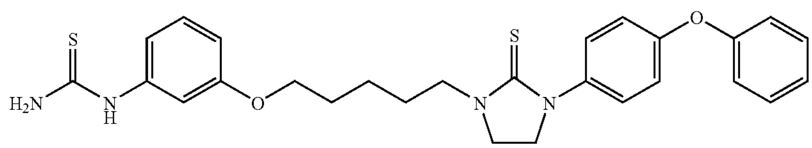 | (3-{5-[3-(4-Phenoxy-phenyl)-2-thioxo-imidazolidin-1-yl]-pentyloxy}-phenyl)-thiourea | 507 |
| 9 | 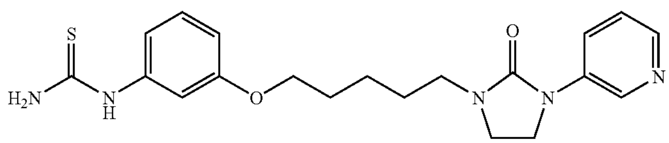 | {3-[5-(2-Oxo-3-pyridin-3-yl-imidazolidin-1-yl)-pentyloxy]-phenyl}-thiourea | 400 |
| 10 | 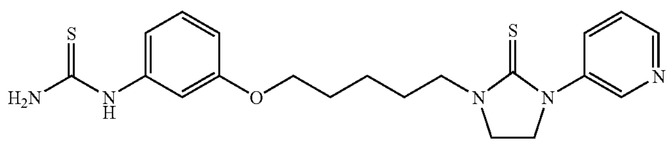 | {3-[5-(3-Pyridin-3-yl-2-thioxo-imidazolidin-1-yl)-pentyloxy]-phenyl}-thiourea | 416 |
| 11 | 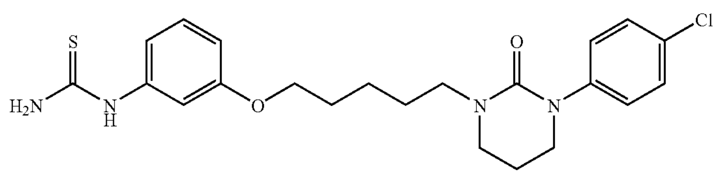 | (3-{5-[3-(4-Chloro-phenyl)-2-oxo-tetrahydro-pyrimidin-1-yl]-pentyloxy}-phenyl)-thiourea | 447 |
| 12 | 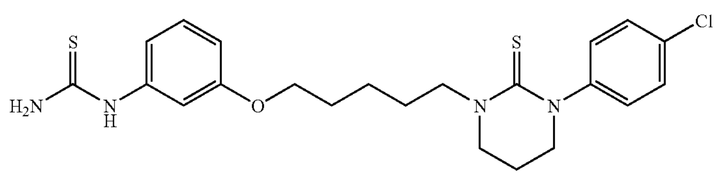 | (3-{5-[3-(4-Chloro-phenyl)-2-thioxo-tetrahydro-pyrimidin-1-yl]-pentyloxy}-phenyl)-thiourea | 463 |
| 13 | 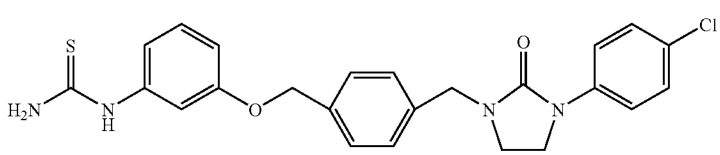 | (3-{4-[3-(4-Chloro-phenyl)-2-oxo-imidazolidin-1-ylmethyl]-benzyloxy}-phenyl)-thiourea | 467 |
| 14 | 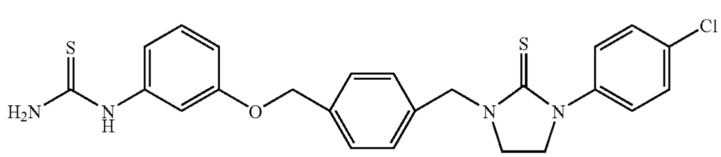 | (3-{4-[3-(4-Chloro-phenyl)-2-thioxo-imidazolidin-1-ylmethyl]-benzyloxy}-phenyl)-thiourea | 483 |
| 15 | 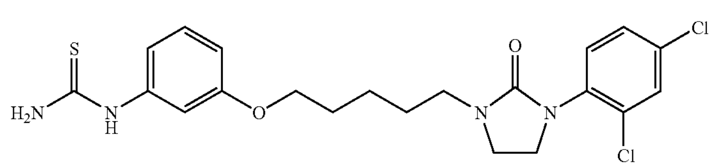 | (3-{5-[3-(2,4-Dichloro-phenyl)-2-oxo-imidazolidin-1-yl]-pentyloxy}-phenyl)-thiourea | 467 |

-continued

| | Structure | Name | M + 1 |
|---|---|---|---|
| 16 | 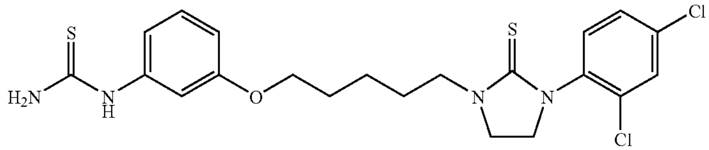 | (3-{5-[3-(2,4-Dichloro-phenyl)-2-thioxo-imidazolidin-1-yl]-pentyloxy}-phenyl)-thiourea | 483 |
| 17 | 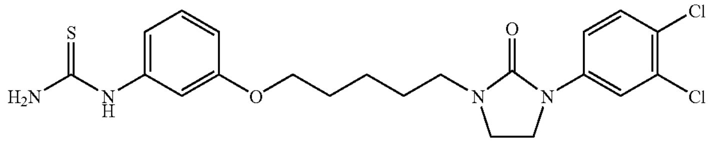 | (3-{5-[3-(3,4-Dichloro-phenyl)-2-oxo-imidazolidin-1-yl]-pentyloxy}-phenyl)-thiourea | 467 |
| 18 | 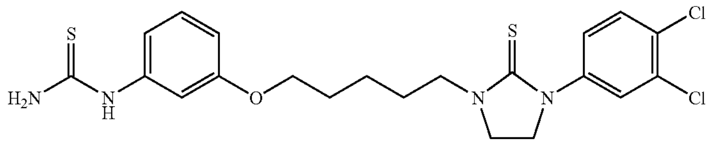 | (3-{5-[3-(3,4-Dichloro-phenyl)-2-thioxo-imidazolidin-1-yl]-pentyloxy}-phenyl)-thiourea | 483 |
| 19 | 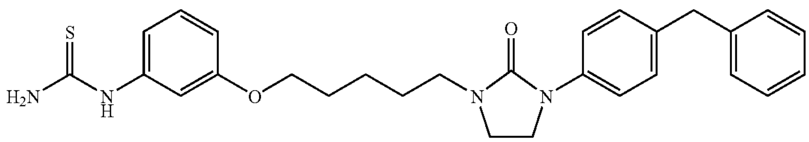 | (3-{5-[3-(4-Benzyl-phenyl)-2-oxo-imidazolidin-1-yl]-pentyloxy}-phenyl)-thiourea | 489 |
| 20 | 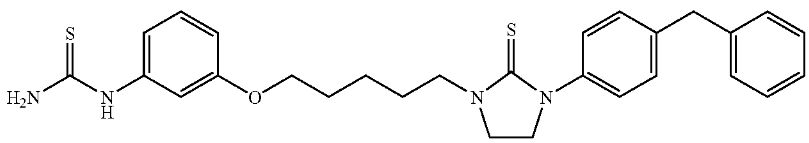 | (3-{5-[3-(4-Benzyl-phenyl)-2-thioxo-imidazolidin-1-yl]-pentyloxy}-phenyl)-thiourea | 505 |
| 21 | 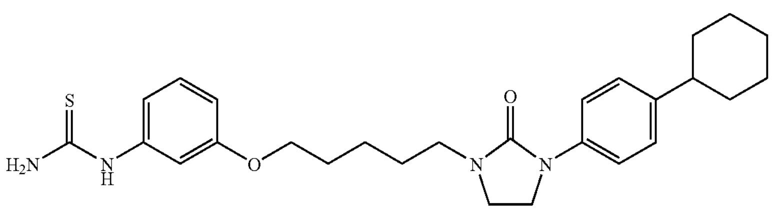 | (3-{5-[3-(4-Cyclohexyl-phenyl)-2-oxo-imidazolidin-1-yl]-pentyloxy}-phenyl)-thiourea | 481 |
| 22 | 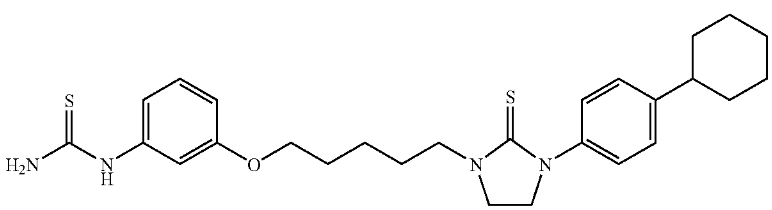 | 3-{5-[3-(4-Cyclohexyl-phenyl)-2-thioxo-imidazolidin-1-yl]-pentyloxy}-phenyl)-thiourea | 497 |
| 23 | 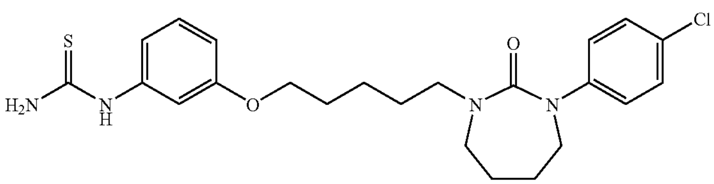 | (3-{5-[3-(4-Chloro-phenyl)-2-oxo-[1,3]diazepan-1-yl]-pentyloxy}-phenyl)-thiourea | 461 |
| 24 | 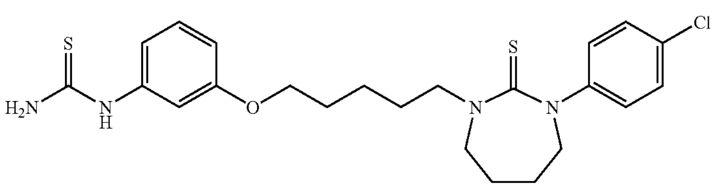 | (3-{5-[3-(4-Chloro-phenyl)-2-thioxo-[1,3]diazepan-1-yl]-pentyloxy}-phenyl)-thiourea | 477 |

| | Structure | Name | M + 1 |
|---|---|---|---|
| 25 | 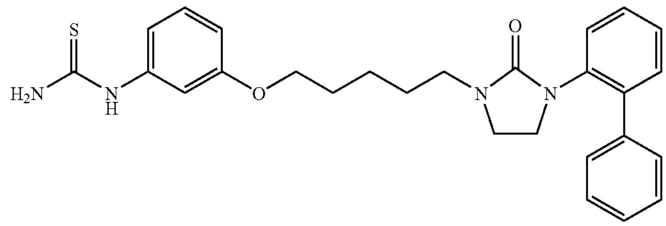 | {3-[5-(3-Biphenyl-2-yl-2-oxo-imidazolidin-1-yl)-pentyloxy]-phenyl}-thiourea | 475 |
| 26 | 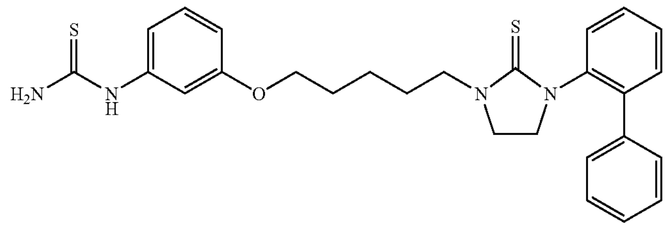 | {3-[5-(3-Biphenyl-2-yl-2-thioxo-imidazolidin-1-yl)-pentyloxy]-phenyl}-thiourea | 491 |

The imidazolidinone and imidazolinethione compounds of this invention can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Schemes 1-3 below show transformations for synthesizing compounds of this invention.

The route shown in Scheme 1 exemplifies synthesis of the imidazolidinone compounds 8 of the present invention. 1,5-Dibromopentane 1 can first react with the 3-nitrophenol in the presence of potassium carbonate in NMP via a substitution reaction to form an alkoxy-containing compound 2. The aryl amine compound 3 is coupled with chloroalkyl isocyanate to afford the corresponding urea intermediate 4. Subsequent intramolecular cyclization of the intermediate 4 by treatment with sodium hydride in the THF/DMF cosolvent system at room temperature results in the formation of cyclic urea 5. Nucleophilic substitution of the cyclic urea 5 with the bromo compound 2 in the presence of sodium hydride in DMF affords compound 6. Subsequent reduction of the nitro group of compound 6 with tin chloride affords the corresponding aryl amine 7. Reaction of the aryl amine 7 with thiocarbonyl diimidazole (TCDI) followed by treatment with 25% aqueous ammonia solution affords the desired imidazolidinone compounds 8.

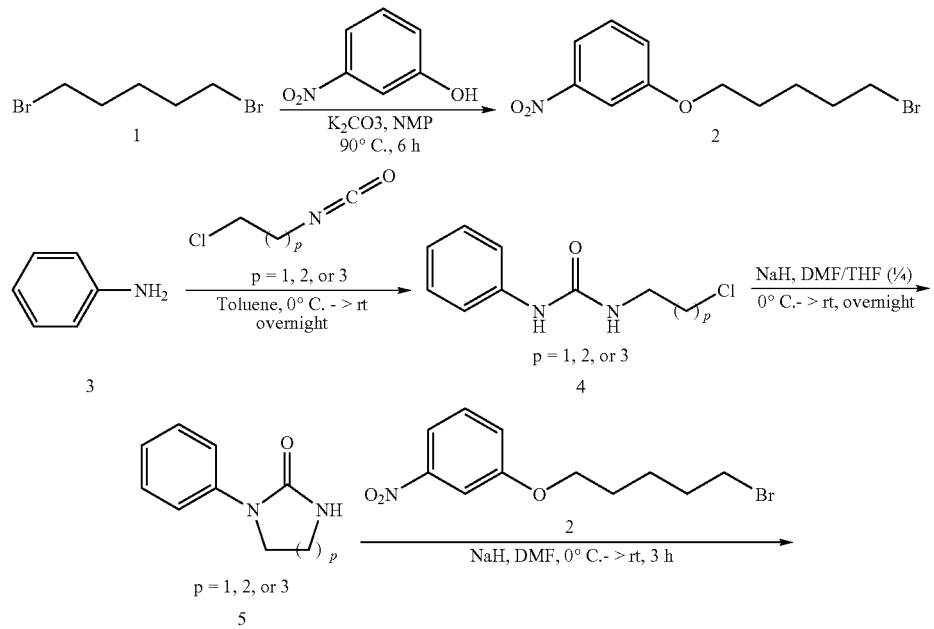

Scheme 1

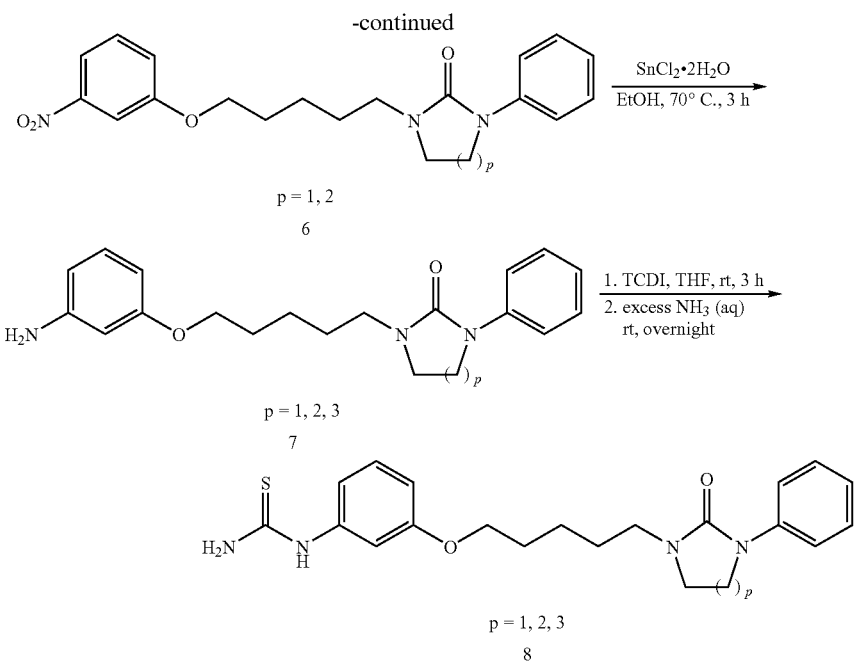

A typical method of preparing the imidazolidinone compounds 15 of the present invention is shown in Scheme 2. The 4-aminobutan-1-ol is coupled with aryl isocyanate 9 to afford the corresponding urea intermediate 10. Tosylation of hydroxyl compound 10 with tosyl chloride in pyridine at room temperature affords the corresponding tosylate 11. Subsequent intramolecular cyclization of the intermediate 11 by treatment with sodium hydride in the THF/DMF cosolvent system at room temperature results in the formation of cyclic urea 12. Nucleophilic substitution of the cyclic urea 12 with the bromo compound 2 in the presence of sodium hydride in DMF gives compound 13. Subsequent reduction of the nitro group of compound 13 with tin chloride affords the corresponding aryl amine 14. Reaction of the aryl amine 14 with thiocarbonyl diimidazole (TCDI) followed by treatment with 25% aqueous ammonia solution gives the desired imidazolidinone compounds 15.

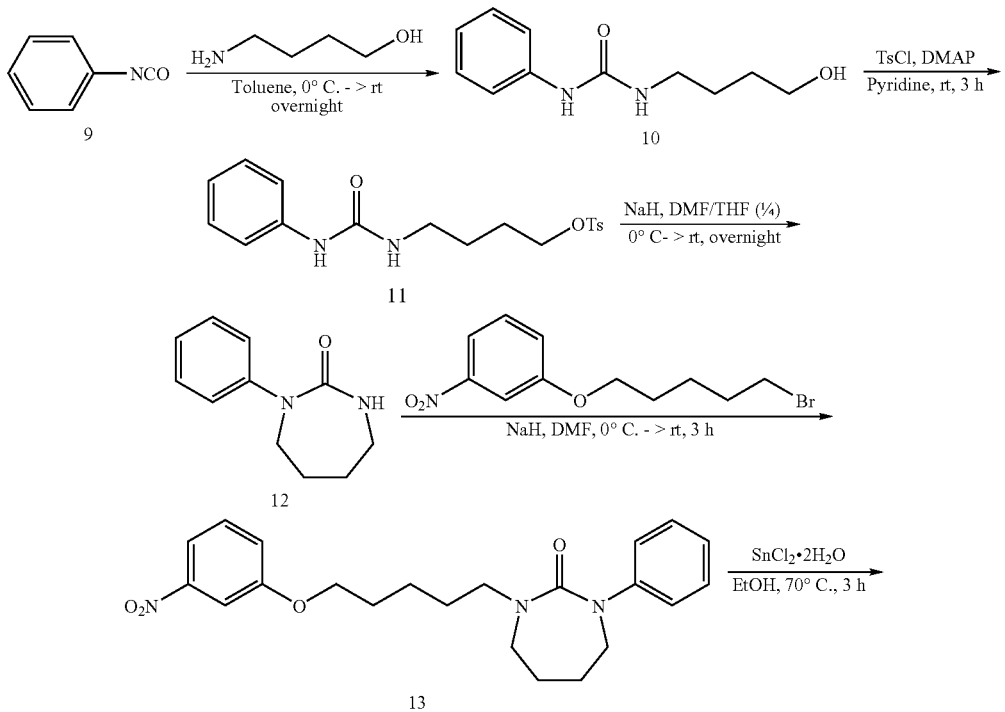

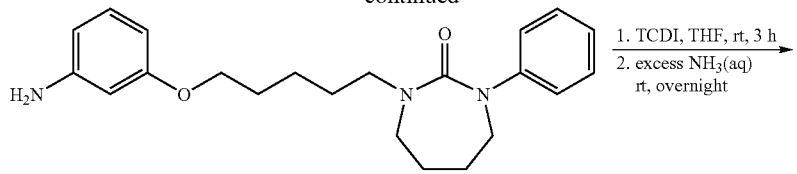

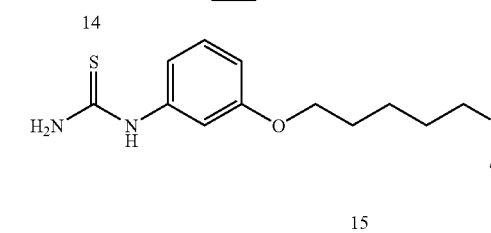

The route shown in Scheme 3 exemplifies synthesis of the imidazolinethione compounds 18 of this invention. The nitro compound (6 or 13) is reacted with phosphorus pentasulfide to afford the corresponding imidazolidinethione compound 16. Subsequent reduction of the imidazolidinethione compound 16 with tin chloride gives the aryl amine 17. Reaction of the aryl amine 17 with thiocarbonyl diimidazole (TCDI) followed by treatment with 25% aqueous ammonia solution affords the desired imidazolinethione compounds 18.

Scheme 3

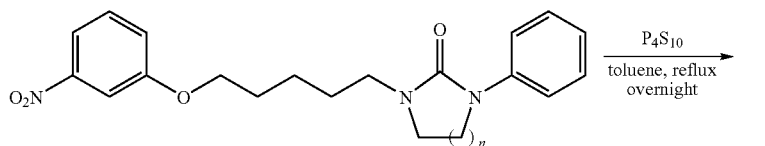

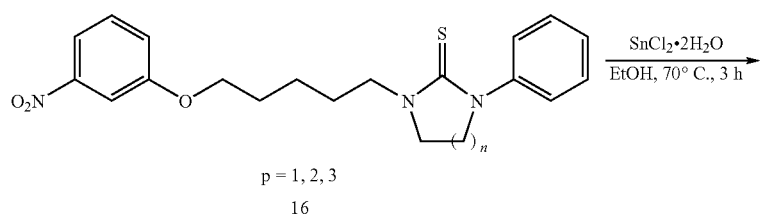

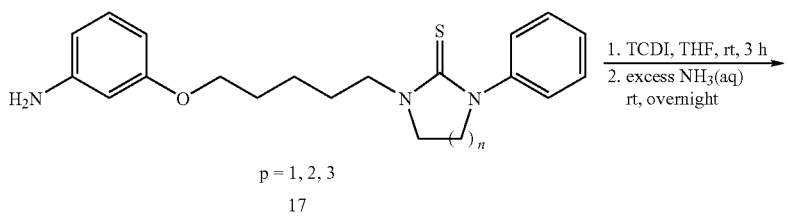

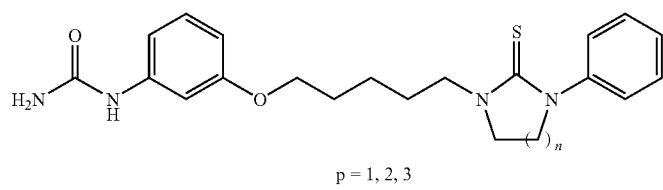

An imidazolidinone or imidazolinethione compound thus synthesized can be further purified by flash column chromatography, high performance liquid chromatography, crystallization, or any other suitable methods.

Also within the scope of this invention are (1) a pharmaceutical composition that contains an effective amount of at least one of the imidazolidinone and imidazolinethione compounds of this invention and a pharmaceutically acceptable carrier, and (2) a method for treating HCV infection by administering to a subject in need of this treatment an effective amount of such an imidazolidinone or imidazolinethione compound.

As used herein, the term "treating" refers to administering an imidazolidinone or imidazolinethione compound to a subject that has HCV infection, or has a symptom of HCV infection, or has a predisposition toward HCV infection, with the purpose to prevent, cure, heal, alleviate, relieve, alter, remedy, ameliorate, improve, or affect the HCV infection, the symptoms of the HCV infection, or the predisposition toward the HCV infection. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An imidazolidinone or imidazolinethione compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, one or more solubilizing agents such as cyclodextrins, which form more soluble complexes with the imidazolidinone or imidazolinethione compounds, can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the imidazolidinone or imidazolinethione compounds of this invention in inhibiting HCV replication. The compounds can further be examined for their efficacy in treating HCV infection. For example, a compound can be administered to an animal (e.g., a mouse model) infected with HCV and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of (3-{5-[3-(4-chloro-phenyl)-2-oxo-imidazolidin-1-yl]-pentyloxy}-phenyl)-thiourea (Compound 1)

Compound 1 was prepared in a manner similar to that outlined in Scheme 1.

Examples 2

Synthesis of (3-{5-[3-(4-chloro-phenyl)-2-thioxo-imidazolidin-1-yl]-pentyloxy}-phenyl)-thiourea (Compound 2)

Compound 2 was prepared in a manner similar to that outlined in Scheme 3.

Example 3

Synthesis of {3-[5-(3-naphthalen-1-yl-2-oxo-imidazolidin-1-yl)-pentyloxy]-phenyl}-thiourea (Compound 3)

Compound 3 was prepared in a manner similar to that outlined in Scheme 1.

Example 4

Synthesis of (3-{7-[3-(4-chloro-phenyl)-2-oxo-imidazolidin-1-yl]-heptyloxy}-phenyl)-thiourea (Compound 5)

Compound 5 was prepared in a manner similar to that outlined in Scheme 1.

Example 5

Synthesis of (3-{5-[2-oxo-3-(4-phenoxy-phenyl)-imidazolidin-1-yl]-pentyloxy}-phenyl)-thiourea (Compound 7)

Compound 7 was prepared in a manner similar to that outlined in Scheme 1.

Example 6

Synthesis of {3-[5-(2-oxo-3-pyridin-3-yl-imidazolidin-1-yl)-pentyloxy]-phenyl}-thiourea (Compound 9)

Compound 9 was prepared in a manner similar to that outlined in Scheme 1.

Example 7

Synthesis of (3-{5-[3-(4-chloro-phenyl)-2-oxo-tetrahydro-pyrimidin-1-yl]-pentyloxy}-phenyl)-thiourea (Compound 11)

Compound 11 was prepared in a manner similar to that outlined in Scheme 1.

Example 8

Synthesis of (3-{4-[3-(4-chloro-phenyl)-2-oxo-imidazolidin-1-ylmethyl]-benzyloxy}-phenyl)-thiourea (Compound 13)

Compound 13 was prepared in a manner similar to that outlined in Scheme 1.

Example 9

Synthesis of (3-{5-[3-(2,4-dichloro-phenyl)-2-oxo-imidazolidin-1-yl]-pentyloxy}-phenyl)-thiourea (Compound 15)

Compound 15 was prepared in a manner similar to that outlined in Scheme 1.

Example 10

Synthesis of (3-{5-[3-(2,4-dichloro-phenyl)-2-thioxo-imidazolidin-1-yl]-pentyloxy}-phenyl)-thiourea (Compound 16)

Compound 16 was prepared in a manner similar to that outlined in Scheme 3.

Example 11

Synthesis of (3-{5-[3-(3,4-dichloro-phenyl)-2-oxo-imidazolidin-1-yl]-pentyloxy}-phenyl)-thiourea (Compound 17)

Compound 17 was prepared in a manner similar to that outlined in Scheme 1.

Example 12

Synthesis of (3-{5-[3-(3,4-dichloro-phenyl)-2-thioxo-imidazolidin-1-yl]-pentyloxy}-phenyl)-thiourea (Compound 18)

Compound 18 was prepared in a manner similar to that outlined in Scheme 3.

Example 13

Synthesis of (3-{5-[3-(4-benzyl-phenyl)-2-oxo-imidazolidin-1-yl]-pentyloxy}-phenyl)-thiourea (Compound 19)

Compound 19 was prepared in a manner similar to that outlined in Scheme 1.

Example 14

Synthesis of (3-{5-[3-(4-cyclohexyl-phenyl)-2-oxo-imidazolidin-1-yl]-pentyloxy}-phenyl)-thiourea (Compound 21)

Compound 21 was prepared in a manner similar to that outlined in Scheme 1.

Example 15

Synthesis of (3-{5-[3-(4-cyclohexyl-phenyl)-2-thioxo-imidazolidin-1-yl]-pentyloxy}-phenyl)-thiourea (Compound 22)

Compound 22 was prepared in a manner similar to that outlined in Scheme 3.

Example 16

Synthesis of (3-{5-[3-(4-chloro-phenyl)-2-oxo-[1,3]diazepan-1-yl]-pentyloxy}-phenyl)-thiourea (Compound 23)

Compound 23 was prepared in a manner similar to that outlined in Scheme 2.

Example 17

Synthesis of {3-[5-(3-biphenyl-2-yl-2-oxo-imidazolidin-1-yl)-pentyloxy]-phenyl}-thiourea (Compound 25)

Compound 25 was prepared in a manner similar to that outlined in Scheme 1.

Example 18

Synthesis of {3-[5-(3-biphenyl-2-yl-2-thioxo-imidazolidin-1-yl)-pentyloxy]-phenyl}-thiourea (Compound 26)

Compound 26 was prepared in a manner similar to that outlined in Scheme 3.

Example 19

Inhibiting HCV Replication

The inhibitory activity of compounds of this invention against HCV replication was assessed using Ava5-EG (Δ4AB)SEAP, a reporter-based cell line, according to the methods described in Lee et al., Anal. Biochem., 316:162-70 (2003) and Lee et al., J. Virol Methods, 116:27-33 (2004). Briefly, Ava5-EG(Δ4AB)SEAP cells were cultured in a medium containing 500 μg/mL G418 (geneticin) and 10 μg/mL blasticidin in a 5% $CO_2$ incubator. G418 and blasticidin were purchased from Invitrogen (Carlsbad, Calif.). The cells were seeded in a 96-well plate ($5\times10^3$ cells/100 μL-well) and incubated at 37° C. for 24 hours. They were then treated with a solution of a test compound in DMSO at various concentrations. After 48 hours, the culture medium in each well was replaced with a fresh medium containing the test compound at the same concentrations to remove secreted alkaline phosphatase accumulated in the culture medium, if any. The cells were cultured for additional 24 hours. The culture medium was then collected and tested for SEAP activity using a Phospha-Light assay kit (Tropix, Foster, Calif., USA). Compounds in Examples 1-18 were tested in this assay. Unexpectedly, 17 of the test compounds showed $EC_{50}$ values (i.e., the concentration of a test compound at which 50% HCV replication is inhibited) lower than 1.5 μM. 14 of them showed even lower $EC_{50}$ values, e.g., lower than 0.5 μM.

Example 20

Cytotoxicity Assay

Viability of cells after treatment (see Example 19 above) was determined by the MTS assay described in Cory et al., Cancer Commun. 3:207-12 (1991). Briefly, Ava5-EG(Δ4AB) SEAP cells were treated with a test compound as described above. After 48 hours, each culture medium was replaced with a fresh medium containing the test compound at the same concentration. The cells were cultured for additional 24 hours. To each well was added 100 μl of a solution containing phenol red-free DMEM, [3-(4,5-dimethylthiozol-2-yl)-5-(3-carboxymethoxyphenyl)-2-(4-sulfophenyl)-2H-tetrazolium, inner salt] (Promega, Madison, Wis.), and phenazine methosulfate (Sigma, St. Louis, Mo.) at a ratio of 80:20:1. The cells were incubated at 37° C. for 1-4 hours in a 5% $CO_2$ incubator. The absorbance at 490 nm in each well was measured. Compounds in Examples 1-18 were tested in this assay. Unexpectedly, all of the test compounds showed $CC_{50}$ values (i.e., the concentration of a test compound at which 50% of the cells are killed) greater than 10 μM and 7 of them showed $CC_{50}$ values greater than 50 μM.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

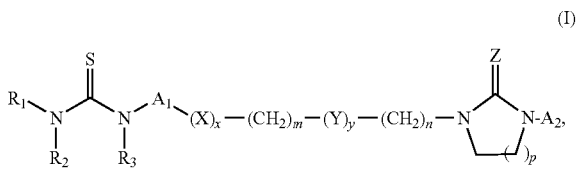

wherein each of $R_1$, $R_2$, and $R_3$, independently, is H, alkyl, alkenyl, alkynyl, cycloalkyl, cycloalkenyl, heterocycloalkyl, heterocycloalkenyl, aryl, or heteroaryl; or $R_1$ and $R_2$, together with the nitrogen atom to which they are bonded, are heterocycloalkyl; or $R_2$ and $R_3$, together with the two nitrogen atoms to which they are bonded and the carbon atom bonded to both of the two nitrogen atoms, are heterocycloalkyl;

$A_1$ is arylene or heteroarylene;

$A_2$ is aryl or heteroaryl;

each of X and Y, independently, is O, S, SO, $SO_2$, $N(R_a)$, $C(R_aR_b)$, C(O), C(O)O, $C(O)NR_a$, $NR_aC(O)NR_b$, $NR_aC(S)NR_b$, $NR_aC(O)O$, $SO_2NR_a$, alkylene, alkenylene, alkynylene, cycloalkylene, heterocycloalkylene, cycloalkenylene, heterocycloalkenylene, arylene, or heteroarylene, in which each of $R_a$ and $R_b$, independently, is H, alkyl, cycloalkyl, heterocycloalkyl, aryl, or heteroaryl;

Z is O or S;

each of m and n, independently, is 0, 1, 2, 3, 4, or 5;

p is 1, 2, or 3;

x is 1; and y is 0 or 1.

2. The compound of claim 1, wherein X is O.

3. The compound of claim 2, wherein $A_1$ is 1,3-phenylene.

4. The compound of claim 3, wherein $A_2$ is phenyl, pyridyl, or naphthyl optionally substituted with halo, alkoxy, aryloxy, alkyl, cycloalkyl, aryl, or heteroaryl.

5. The compound of claim 4, wherein each of $R_1$, $R_2$, and $R_3$ is H.

6. The compound of claim 5, wherein Y is 1,4-phenylene; and y is 0 or 1.

7. The compound of claim 1, wherein $A_1$ is 1,3-phenylene; and $A_2$ is phenyl, pyridyl, or naphthyl optionally substituted with halo, alkoxy, aryloxy, alkyl, cycloalkyl, aryl, or heteroaryl.

8. The compound of claim 7, wherein each of $R_1$, $R_2$, and $R_3$ is H.

9. The compound of claim 1, wherein the compound is one of the following compounds:
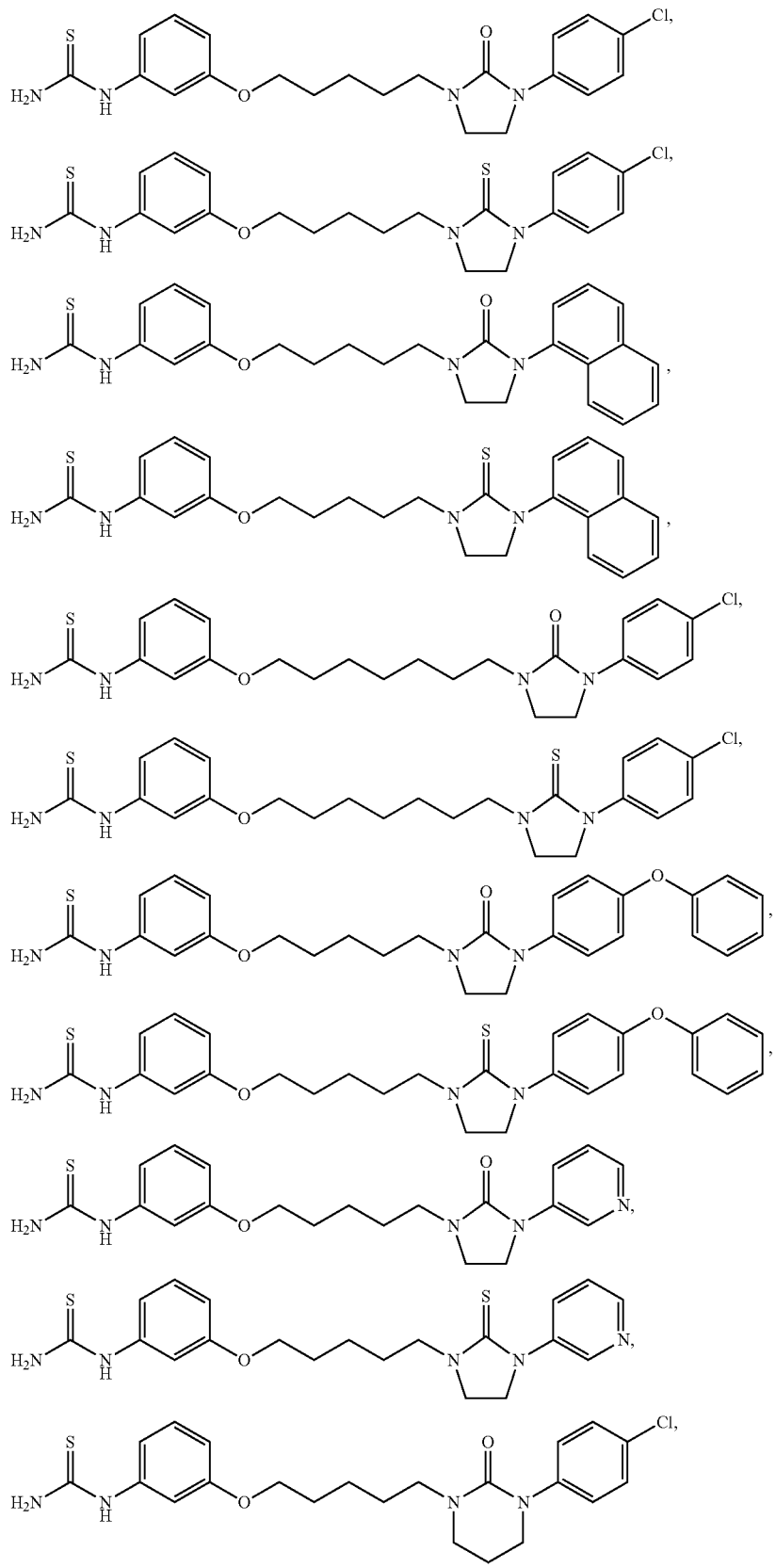

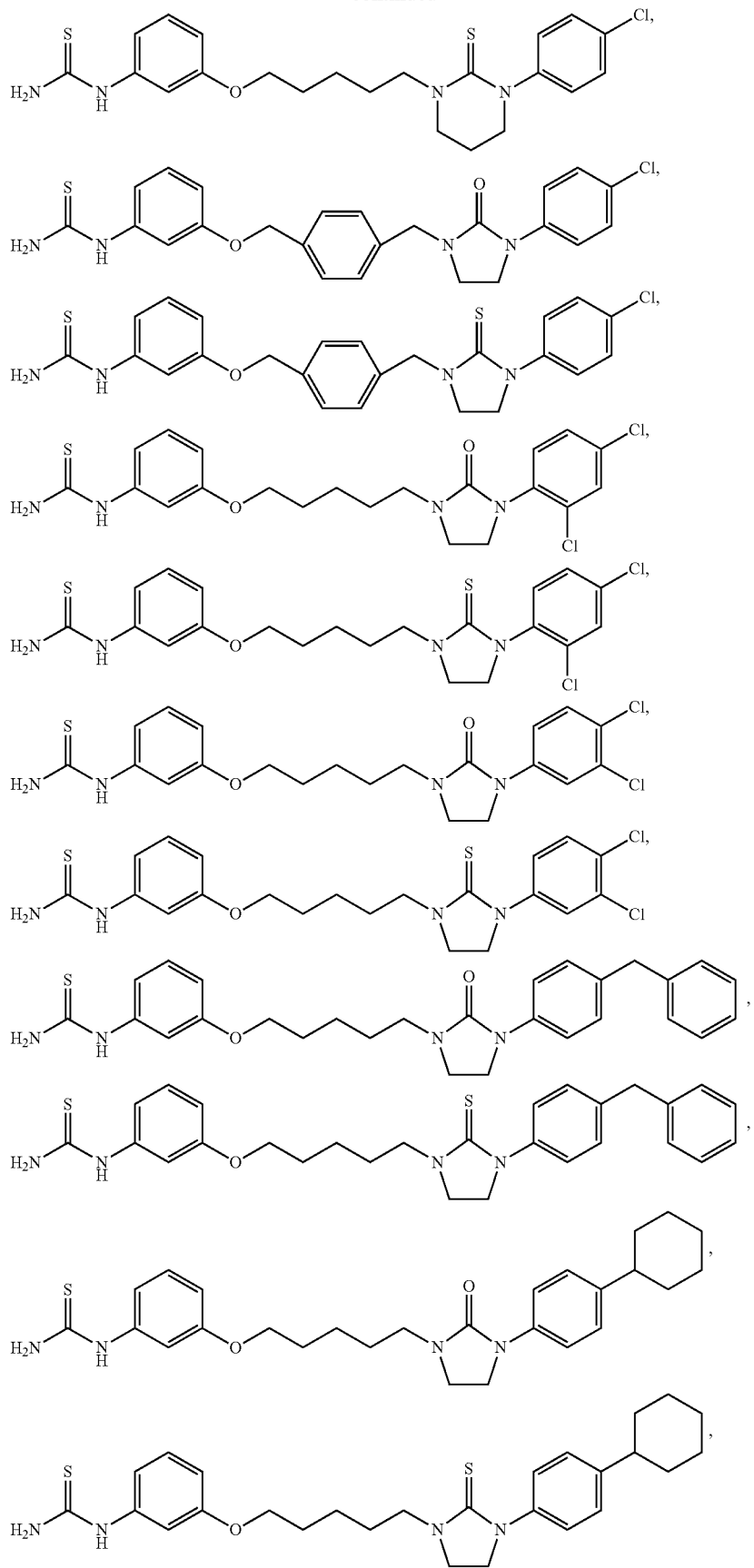

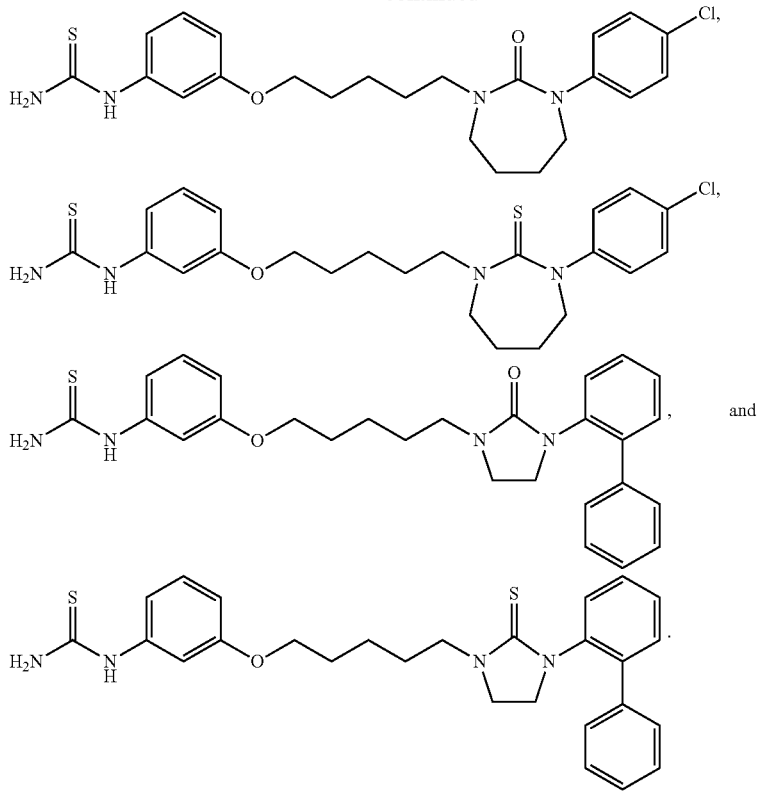

10. A method for treating hepatitis C virus infection, comprising administering to a subject in need thereof an effective amount of a compound of formula (I):

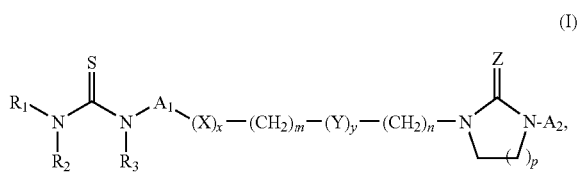

wherein
each of $R_1$, $R_2$, and $R_3$, independently, is H, alkyl, alkenyl, alkynyl, cycloalkyl, cycloalkenyl, heterocycloalkyl, heterocycloalkenyl, aryl, or heteroaryl; or $R_1$ and $R_2$, together with the nitrogen atom to which they are bonded, are heterocycloalkyl; or $R_2$ and $R_3$, together with the two nitrogen atoms to which they are bonded and the carbon atom bonded to both of the two nitrogen atoms, are heterocycloalkyl;
$A_1$ is arylene or heteroarylene;
$A_2$ is aryl or heteroaryl;
each of X and Y, independently, is O, S, SO, $SO_2$, $N(R_a)$, $C(R_aR_b)$, C(O), C(O)O, $C(O)NR_a$, $NR_aC(O)NR_b$, $NR_aC(S)NR_b$, $NR_aC(O)O$, $SO_2NR_a$, alkylene, alkenylene, alkynylene, cycloalkylene, heterocycloalkylene, cycloalkenylene, heterocycloalkenylene, arylene, or heteroarylene, in which each of $R_a$ and $R_b$, independently, is H, alkyl, cycloalkyl, heterocycloalkyl, aryl, or heteroaryl;
Z is O or S;
each of m and n, independently, is 0, 1, 2, 3, 4, or 5;
p is 1, 2, or 3; and
each of x and y, independently, is 0 or 1.

11. The method of claim 10, wherein X is O and x is 1.

12. The method of claim 11, wherein $A_1$ is 1,3-phenylene.

13. The method of claim 12, wherein $A_2$ is phenyl, pyridyl, or naphthyl optionally substituted with halo, alkoxy, aryloxy, alkyl, cycloalkyl, aryl, or heteroaryl.

14. The method of claim 13, wherein each of $R_1$, $R_2$, and $R_3$ is H.

15. The method of claim 14, wherein Y is 1,4-phenylene and; y is 0 or 1.

16. The method of claim 10, wherein $A_1$ is 1,3-phenylene; and $A_2$ is phenyl, pyridyl, or naphthyl optionally substituted with halo, alkoxy, aryloxy, alkyl, cycloalkyl, aryl, or heteroaryl.

17. The method of claim 16, wherein each of $R_1$, $R_2$, and $R_3$ is H.

18. A pharmaceutical composition, comprising a compound of claim 1 and a pharmaceutically acceptable carrier.

19. The composition of claim 18, wherein X is O and x is 1.

20. The composition of claim 19, wherein $A_1$ is 1,3-phenylene.

21. The composition of claim 20, wherein $A_2$ is phenyl, pyridyl, or naphthyl Optionally substituted with halo, alkoxy, aryloxy, alkyl, cycloalkyl, aryl, or heteroaryl.

22. The composition of claim 21, wherein each of $R_1$, $R_2$, and $R_3$ is H.

23. The composition of claim 22, wherein Y is 1,4-phenylene and; y is 0 or 1.

24. The composition of claim 19, wherein $A_1$ is 1,3-phenylene; and $A_2$ is phenyl, pyridyl, or naphthyl optionally substituted with halo, alkoxy, aryloxy, alkyl, cycloalkyl, aryl, or heteroaryl.

25. The composition of claim 24, wherein each of $R_1$, $R_2$, and $R_3$ is H.

26. A compound of formula (I):

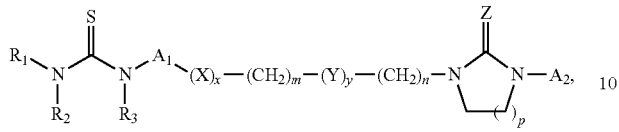

wherein
each of $R_1$, $R_2$, and $R_3$, independently, is H, alkyl, alkenyl, alkynyl, cycloalkyl, cycloalkenyl, heterocycloalkyl, heterocycloalkenyl, aryl, or heteroaryl; or $R_1$ and $R_2$, together with the nitrogen atom to which they are bonded, are heterocycloalkyl; or $R_2$ and $R_3$, together with the two nitrogen atoms to which they are bonded and the carbon atom bonded to both of the two nitrogen atoms, are heterocycloalkyl;
$A_1$ is arylene or heteroarylene;
$A_2$ is aryl or heteroaryl;
each of X and Y, independently, is O, S, SO, $SO_2$, $N(R_a)$, $C(R_aR_b)$, C(O), C(O)O, $C(O)NR_a$, $NR_aC(O)NR_b$, $NR_aC(S)NR_b$, $NR_aC(O)O$, $SO_2NR_a$, alkylene, alkenylene, alkynylene, cycloalkylene, heterocycloalkylene, cycloalkenylene, heterocycloalkenylene, arylene, or heteroarylene, in which each of $R_a$ and $R_b$, independently, is H, alkyl, cycloalkyl, heterocycloalkyl, aryl, or heteroaryl;
Z is O or S;
m is 1, 2, 3, 4, or 5;
n is 0, 1, 2, 3, 4, or 5;
p is 1, 2, or 3; and
each of x and y, independently, is 0 or 1.

27. A compound of formula (I):

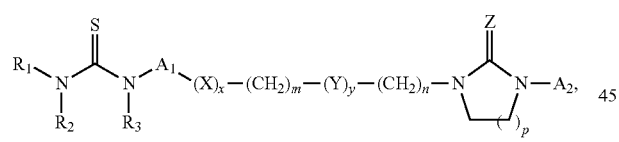

wherein
each of $R_1$, $R_2$, and $R_3$, independently, is H, alkyl, alkenyl, alkynyl, cycloalkyl, cycloalkenyl, heterocycloalkyl, heterocycloalkenyl, aryl, or heteroaryl; or $R_1$ and $R_2$, together with the nitrogen atom to which they are bonded, are heterocycloalkyl; or $R_2$ and $R_3$, together with the two nitrogen atoms to which they are bonded and the carbon atom bonded to both of the two nitrogen atoms, are heterocycloalkyl;
$A_1$ is arylene or heteroarylene;
$A_2$ is aryl or heteroaryl;
each of X and Y, independently, is O, S, SO, $SO_2$, $N(R_a)$, $C(R_aR_b)$, C(O), C(O)O, $C(O)NR_a$, $NR_aC(O)NR_b$, $NR_aC(S)NR_b$, $NR_aC(O)O$, $SO_2NR_a$, alkylene, alkenylene, alkynylene, cycloalkylene, heterocycloalkylene, cycloalkenylene, heterocycloalkenylene, arylene, or heteroarylene, in which each of $R_a$ and $R_b$, independently, is H, alkyl, cycloalkyl, heterocycloalkyl, aryl, or heteroaryl;
Z is O or S;
m is 0, 1, 2, 3, 4, or 5;
n is 1, 2, 3, 4, or 5;
p is 1, 2, or 3; and
each of x and y, independently, is 0 or 1.

28. A compound of formula (I):

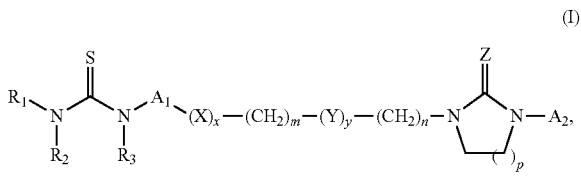

wherein
each of $R_1$, $R_2$, and $R_3$, independently, is H, alkyl, alkenyl, alkynyl, cycloalkyl, cycloalkenyl, heterocycloalkyl, heterocycloalkenyl, aryl, or heteroaryl; or $R_1$ and $R_2$, together with the nitrogen atom to which they are bonded, are heterocycloalkyl; or $R_2$ and $R_3$, together with the two nitrogen atoms to which they are bonded and the carbon atom bonded to both of the two nitrogen atoms, are heterocycloalkyl;
$A_1$ is arylene or heteroarylene;
$A_2$ is aryl or heteroaryl;
each of X and Y, independently, is O, S, SO, $SO_2$, $N(R_a)$, $C(R_aR_b)$, C(O), C(O)O, $C(O)NR_a$, $NR_aC(O)NR_b$, $NR_aC(S)NR_b$, $NR_aC(O)O$, $SO_2NR_a$, alkylene, alkenylene, alkynylene, cycloalkylene, heterocycloalkylene, cycloalkenylene, heterocycloalkenylene, arylene, or heteroarylene, in which each of $R_a$ and $R_b$, independently, is H, alkyl, cycloalkyl, heterocycloalkyl, aryl, or heteroaryl;
Z is O or S;
each of m and n, independently, is 0, 1, 2, 3, 4, or 5;
p is 1, 2, or 3;
x is 0 or 1; and
y is 1.

* * * * *